United States Patent [19]
Lin et al.

[11] Patent Number: 4,579,978
[45] Date of Patent: Apr. 1, 1986

[54] BIBENZYL HYDROPEROXIDE SYNTHESIS
[75] Inventors: Jiang-Jen Lin, Round Rock; John R. Sanderson, Austin, both of Tex.
[73] Assignee: Texaco Inc., White Plains, N.Y.
[21] Appl. No.: 670,102
[22] Filed: Nov. 13, 1984
[51] Int. Cl.$^4$ .................................................. C07C 179/035
[52] U.S. Cl. .................... 568/573; 568/565; 568/569
[58] Field of Search ............... 568/564, 565, 568, 574, 568/573, 569, 561

[56] References Cited

U.S. PATENT DOCUMENTS

| | | | |
|---|---|---|---|
| 2,577,768 | 12/1951 | Joris | 568/574 |
| 3,775,472 | 11/1973 | Massie | 568/431 |
| 4,262,143 | 4/1981 | Becker | 568/574 |

OTHER PUBLICATIONS

Pryor et al, J. Org. Chem., vol. 43, No. 4, pp. 770-772, (1978).
Sergienko et al I, Chemical Abstracts, vol. 51, No. 14634f, 1957.
Sergienko et al II, Chemical Abstracts, vol. 53, No. 21080d, 1959.
Sergeev et al, Chemical Abstracts, vol. 55, No. 18660e, 1961.
Pikaeva et al, Chemical Abstacts, vol. 58, No. 2876a, 1963.

Primary Examiner—Natalie Trousof
Assistant Examiner—Bruce D. Gray
Attorney, Agent, or Firm—Jack H. Park; Kenneth R. Priem

[57] ABSTRACT

Substantially quantitative yields of bibenzyl hydroperoxide and bibenzyl dihydroperoxide can be obtained when oxygen is reacted with bibenzyl (1,2-diphenylethane) in the presence of a minor amount of sodium bicarbonate at a temperature within the range of about 100° to about 160° C. to provide an oxidation product wherein the bibenzyl is substantially selectively converted to the bibenzyl hydroperoxides. The bibenzyl hydroperoxides can be used as raw materials for the production of propylene oxide by reacting the bibenzyl hydroperoxides with propylene.

3 Claims, No Drawings

BIBENZYL HYDROPEROXIDE SYNTHESIS

BACKGROUND OF THE INVENTION

1. Field of the Invention

This invention relates to a method for the synthesis of bibenzyl hydroperoxides. More particularly, this invention relates to a method for the oxidation of bibenzyl under conditions which substantially selectively promote the oxidation of the bibenzyl to bibenzyl hydroperoxides. In yet another aspect, the present invention is directed to the synthesis of a new compound, bibenzyl dihydroperoxide.

2. Prior Art

Massie U.S. Pat. No. 3,775,472, which issued Nov. 27, 1973, is directed to oxidizing alkyl aromatic hydrocarbons with oxygen in the presence of a catalyst comprising a ruthenium-containing compound to thereby form oxygenated aromatic compounds, including hydroperoxides.

Becker U.S. Pat. No. 4,262,143, which issued Apr. 14, 1981, is directed to a process for the preparation of ethylbenzene hydroperoxide wherein ethylbenzene is reacted with molecular oxygen in the presence of a small amount of a hydroxide or salt of sodium or potassium.

There is an article by William A. Pryor in the *Journal of Organic Chemistry*, Volume 43, No. 4, 1978, on pages 770-772 which is entitled "The Chemistry of Benzyl Hydroperoxide" which points out that benzyl hydroperoxide can be formed by air oxidation of 5-methylene-1,3-cyclohexadiene in solution in a trichloromethane solvent.

RELATED COPENDING PATENT APPLICATION

Copending coassigned Lin et al. U.S. patent application Ser. No. 06/670,101, filed Nov. 13, 1984 (filed of an even date herewith) (Docket No. 80,337) discloses a process wherein bibenzyl is oxidized under conditions which selectively promote the oxidation of the bibenzyl to bibenzyl hydroperoxides and the bibenzyl hydroperoxides are then catalytically reacted with propylene to provide propylene oxide and the hydroxy-substituted analoges of the bibenzyl hydroperoxides.

SUMMARY OF THE INVENTION

It has been surprisingly discovered, in accordance with the present invention, that substantially quantitative yields of bibenzyl hydroperoxide and bibenzyl dihydroperoxide can be obtained when oxygen is reacted with bibenzyl (1,2-diphenylethane) under the controlled oxidation conditions of the present invention. In accordance with the present invention, bibenzyl is oxidized with oxygen in the presence of a minor amount of sodium bicarbonate at a temperature within the range of about 100° to about 160° C. to provide an oxidation product wherein the bibenzyl is substantially selectively converted to the bibenzyl hydroperoxides. The bibenzyl hydroperoxides can be used as raw materials for the production of propylene oxide by reacting the bibenzyl hydroperoxides and propylene.

The starting materials for the present invention include bibenzyl, oxygen, sodium bicarbonate and a suitable oxidization initiator such as di-t-butyl hydroperoxide.

The oxygen may be employed as such, or may be supplied by bringing air or any other appropriate mixture of oxygen and inert gases into contact with the bibenzyl.

The sodium bicarbonate is suitably employed in an amount within the range of about 0.1 to about 2 wt. %, based upon the bibenzyl, and, more preferably, within the range of about 0.4 to about 1.2 wt. %.

The reaction is suitably conducted at a temperature within the range of about 100° to about 180°, such as a temperature within the range of about 120° to about 150° C.

Reaction times may vary within from about 1 to about 10 hours, depending upon the degree of conversion that is desired.

The oxygen pressure employed in the reaction is suitably within the range of about 1 to about 10 atmospheres. It is preferred to disperse oxygen in the reaction mixture at 1 atmosphere to provide good liquid-gas mixing. A reaction initiator, such as di-t-butyl peroxide, di-t-butyl peroxybenzoate or other peroxides, is optionally used in a trace amount to initiate the reaction in accordance with well known prior art procedures.

At the end of the reaction, the bibenzyl hydroperoxides may be recovered from unreacted bibenzyl and other reaction product components by any suitable procedure such as vacuum distillation, solvent extraction, crystallization, etc.

An important feature of the present invention is the use of sodium bicarbonate. It has been discovered in accordance with the present invention that when bibenzyl is oxidized by air in the absence of sodium bicarbonate, the bibenzyl is converted in large measure to oxidation products other than the bibenzyl hydroperoxides, such as benzaldehyde, benzoic acid, benzyl alcohol, etc.

DETAILED DESCRIPTION OF THE PREFERRED EMBODIMENT OF THE PRESENT INVENTION

The present invention is further illustrated by the following specific examples which are given by way of illustration and which are not intended as limitations on the scope of this invention.

EXAMPLE 1

(Comparative)

To a glass reactor was charged bibenzyl (20 g) and 10 drops of di-t-butyl peroxide. The mixture was heated to 130° C., while agitating with a magnetic stirrer. Then air was bubbled through the liquid mixture at the rate of ca. 50 ml/min. An aliquot of sample was taken at the period of reaction time of 3.5 hr. and 5.5 hr. The analyses of H-nmr have shown the following results.

At 3.5 hr. reaction time, the conversion of bibenzyl was less than 5%. At 5.5 hr. reaction time, the conversion of bibenzyl was ca. 6%. The product selectivities were calculated to be:

| (I) | 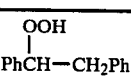 | bibenzyl monohydroperoxide | 43% molar |
| --- | --- | --- | --- |
| (II) | 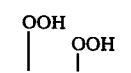 | bibenzyl dihydroperoxide | 10% |
| (III) | 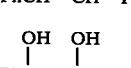 | 1,2-diphenyl ethylene glycol | 13% |

| | | | |
|---|---|---|---|
| (IV) | PhCHO | benzaldehyde | 24% |
| (V) | PhCH$_2$OH | benzyl alcohol | 10% |

EXAMPLE 2

(Comparative)

The similar experimental procedures as Example 1 were used. The reactor was charged with bibenzyl 50 g. With air bubbling at the rate of ca. 50 ml/min, the mixture was heated at 120° C. for ca. 5 hr. and at 130°–135° C. for four hours and 45 minutes. The final reaction mixture was analyzed by H-nmr and shown the following results:

The conversion of bibenzyl was ca. 20%.
The selectivities to the following products were:
(I) 53%
(II) 13%
(III) 13%
(IV) 15%
(V) 5% .

EXAMPLE 3

The same procedures as Example 1 were used.

The reactor was charged with bibenzyl 40 g, sodium bicarbonate (0.20 g) and 10 drops of di-t-butyl peroxide. The reaction conditions were at 128°–133° C. for 2.0 hr. under the air flow rate of ca. 50 ml/min. The results are shown:

8% conversion of bibenzyl
94% selectivity to (I) bibenzyl monohydroperoxide
~6% selectivity to (II) bibenzyl dihydroperoxide.

It is realized that the addition of sodium bicarbonate (~0.5%) affected both the reaction rate and the product selectivity. The very high selectivity to the hydroperoxide I and II was achieved.

EXAMPLE 4

The same procedures as Experiment 1 were used.

The mixtures of bibenzyl (20 g), sodium bicarbonate (0.1 g) and 10 drops of di-t-butyl peroxide were subjected to air flow at rate of ca. 50 ml/min. and 130°–140° C. for 3 hours.

The conversion of bibenzyl was ~13%.
The selectivities to the desired products were considered high.
(I) 80–85%
(II) trace
(III) ~15%
(IV) trace
(V) 0 .

The product selectivity to (I) was slightly decreased compared to Example 3 at a higher conversion level.

EXAMPLE 5

The same reaction procedures were used except sodium carbonate instead of sodium bicarbonate was used.

The mixtures of bibenzyl 20 g, sodium carbonate 0.40 g and 20 drops of di-t-butyl peroxide were exposed to the air flow of ca. 50 ml/min at 130°–133° C. for a total of 10 hours reaction time. At 4 hr. reaction time, the portion of sample showed only <5% conversion of bibenzyl. The sample at 10 hours reaction indicated the following result:

30% conversion of bibenzyl and
80% selectivity to benzoic acid
~20% selectivity to benzaldehyde The presence of sodium carbonate showed the different product formation, with benzoic acid and benzaldehyde as predominant products.

EXAMPLE 6

The same experimental procedures were used, except tetra-n-butylammonium bromide was used instead of NaHCO$_3$. The reaction conditions were 118°–120° C., 7 hours and air flow rate at ca. 50 ml/min.

The analysis showed that:

11% conversion of bibenzyl $$\text{0\% selectivity to (I) PhCH}\underset{|}{\overset{\text{OOH}}{\text{—}}}\text{CH}_2\text{Ph}$$

$$\text{0\% selectivity to (II) PhCH}\underset{|}{\overset{\text{OOH}}{\text{—}}}\text{—}\underset{|}{\overset{\text{OOH}}{\text{CH}}}\text{—Ph}$$

$$\text{17\% selectivity to (III) PhCH}\underset{|}{\overset{\text{OH}}{\text{—}}}\underset{|}{\overset{\text{OH}}{\text{CH}}}\text{—Ph}$$

43% selectivity to (IV) PhCHO
13% selectivity to (V) PhCH$_2$OH $$\text{26\% selectivity to (VI) PhCH}\underset{|}{\overset{\text{OH}}{\text{—}}}\text{CH}_2\text{Ph}$$

Having thus described our method for the synthesis of bibenzyl hydroperoxides, we now set forth the subject matter that we claim as our invention in the following claims.

What is claimed is:

1. A method for the preparation of bibenzyl hydroperoxide which comprises contacting bibenzyl with oxygen in the presence of sodium bicarbonate to thereby substantially inhibit the formation of bibenzyl dihydroperoxide and to provide a reaction product comprising a predominant amount of bibenzyl hydroperoxide, and recovering bibenzyl hydroperoxide from said reaction product.

2. A method as in claim 1, wherein the oxygen is brought into contact with the bibenzyl under reaction conditions including a temperature within the range of about 100° to about 160° C. and a reaction time within the range of about 1 to about 10 hours.

3. A method as in claim 2, wherein the sodium bicarbonate is initially present in the reaction mixture in an amount within the range of about 0.1 to about 2 wt. %, based on the bibenzyl, and wherein the reaction temperature is within the range of about 120° to about 150° C.

* * * * *